United States Patent [19]

Bolanos et al.

[11] Patent Number: 5,575,799
[45] Date of Patent: Nov. 19, 1996

[54] ARTICULATING SURGICAL APPARATUS

[75] Inventors: Henry Bolanos, East Norwalk; Frank J. Viola, Sandy Hook, both of Conn.

[73] Assignee: United States Surgical Corporation, Norwalk, Conn.

[21] Appl. No.: 413,296

[22] Filed: Mar. 30, 1995

[51] Int. Cl.$^6$ .................................................. A61B 17/00
[52] U.S. Cl. ........................ 606/139; 606/142; 606/208; 227/175.1
[58] Field of Search ..................... 606/205–208, 606/142, 143, 139, 180, 198; 227/175–182, 901–19; 604/95, 280, 283; 433/103, 108, 109, 124, 126, 127, 130, 133; 285/184, 118

[56] References Cited

U.S. PATENT DOCUMENTS

| | | | |
|---|---|---|---|
| 597,469 | 1/1898 | Marshall | 433/124 |
| 1,677,337 | 7/1928 | Grove | 606/180 |
| 2,507,710 | 5/1950 | Grosso . | |
| 2,557,507 | 6/1951 | Lang | 285/184 |
| 2,886,262 | 5/1959 | Fletcher | 285/184 |
| 3,742,957 | 7/1973 | White . | |
| 5,234,460 | 8/1993 | Stouder, Jr. . | |
| 5,275,608 | 1/1994 | Forman et al. . | |
| 5,282,800 | 2/1994 | Foshee et al. . | |
| 5,289,963 | 3/1994 | McGarry et al. . | |
| 5,289,964 | 3/1994 | Yoneyama et al. . | |
| 5,352,234 | 10/1994 | Scott | 433/133 |
| 5,431,323 | 7/1995 | Smith et al. | 227/177 |

FOREIGN PATENT DOCUMENTS

| | | |
|---|---|---|
| WO9400059 | 1/1994 | WIPO . |
| WO9404084 | 3/1994 | WIPO . |

OTHER PUBLICATIONS

DaVinci Medical promotional material entitled, "Experience the Movement", 1994.

*Primary Examiner*—Michael Powell Buiz
*Assistant Examiner*—Jeffrey A. Schmidt

[57] ABSTRACT

An apparatus for use in minimally invasive surgery includes a articulating segmented endoscopic portion wherein the segments are connected by an angled rotary interface. Rotation of the distal segment moves the distal segment to a position which is angled relative to the proximal segment. A handle grip portion may be likewise articulated.

21 Claims, 8 Drawing Sheets

Fig. 11

ARTICULATING SURGICAL APPARATUS

BACKGROUND

1. Field of the Invention

The present device relates to a surgical apparatus, e.g., for applying surgical staples to body tissue and to attach objects to body tissue. More particularly, the device described herein is preferably useful in minimally invasive surgical procedures and provides advantageous articulating features.

2. Background

Surgical repair of body organs an tissue often requires the application of surgical fasteners. In some instances, the fasteners used are in the form of two part fasteners and in other instances, they are unitary metal staples. Such metal staples are used in numerous types of body tissue repair including such procedures as chest wall reconstructions, tram flap procedures, hernia repairs, etc. In most surgical repairs, the staples are applied directly to the body tissue requiring attachment or reattachment. In certain other procedures, the staples are used to attach an intermediate object to the body tissue. One such example is the application of surgical mesh to body tissue which is often used in hernia repairs.

For example, the surgical repair of hernias is generally confined to the lower abdominal and groin areas of the body, involving repositioning reattachment of the herniated portion of the abdomen using surgical staples or sutures. Developments in minimally invasive surgical procedures, such as laparoscopic and endoscopic surgery, have enabled surgical procedures to be performed in certain confined areas. In addition, surgical repairs involving other body parts or organs have also benefitted from laparoscopic and endoscopic advances.

Minimally invasive surgical procedures involve the deployment of instrumentation through small openings in a wall of body tissue. This type of surgery is highly advantageous because trauma to the patient is substantially reduced, which also reduces recovery time, costs, and the risk of post-operative complications. For convenience, as hereinafter used the term "endoscopic" shall refer generally to all types of minimally invasive surgical procedures, including laparoscopic procedures.

An endoscopic instrument is one which provides the facility for a surgeon to operate at a site in the interior of a patient's body while actuating the instrument exterior to the body. Endoscopic instruments have a relatively long endoscopic portion which is sufficiently narrow to be inserted through a trocar cannula or small entrance incision in the skin. An operating portion is positioned at the distal end of the endoscopic portion and may include such devices as clip or staple appliers, graspers, tissue movers, and the like. Actuation of the instrument is accomplished outside the body, remote from the operating site. Typically, the endoscopic instrument has a non-endoscopic handle portion having actuators such as triggers, push buttons, rotary dials, and the like. In the endoscopic portion of the apparatus, movement of internal working members, such as drive rods, camming members, and the like is generally constrained to linear motion along or parallel to the longitudinal axis of the instrument, or to rotation around the axis. The distal operating portion may additionally have some lateral component or motion, such as, for example, the jaws which pivot laterally to open or close. Typically, there must be a fluid seal within the apparatus and between the apparatus and cannula to prevent entry or egress of fluids. This is especially true in abdominal surgery wherein the abdominal cavity is insufflated with a gas. Sealing can be provided by having close tolerances between moving parts, or by having sealing members.

One elongated surgical stapler for endoscopic applications is described in commonly assigned U.S. patent application No. 07/950,425, filed on Sep. 21, 1992 now abandoned which is incorporated herein by reference. The aforesaid elongated surgical stapler comprises frame means, generally elongated endoscopic means, means for storing a surgical staple, means for individually advancing the staple distally, and anvil means for closing the staple to engage the staple into body tissue.

Non-endoscopic hernia procedures may also entail surgery in the confined areas of the lower or upper abdomen. Instruments which are relatively short in length may be utilized for direct insertion into the lower abdomen through surgical incisions. It would be advantageous to provide a surgical stapler whereby the distal end of the stapler articulates relative to an axis of the stapler after the stapler is inserted for extending the distal end around bones, body tissue, and the like to orient and apply surgical staples from the distal end into body tissue. These staples could be applied directly to body tissue or for attaching objects such as mesh to body tissue.

Therefore, a need exists in many such procedures for a compact surgical stapler having an articulating distal end for accurately positioning and securely attaching surgical staples to body tissue. In addition, the articulation mechanism should provide a stable articulated position at the distal end, allowing the distal end to be set in a fixed orientation by the operator, freeing the operator's hands for other activities.

Moreover, it would be highly advantageous for the handle portion to articulate as well. Articulation of the handle portion would provide for adaptability to accommodate different methods of holding and handling the apparatus during operation and would be a great convenience to the operating personnel.

SUMMARY

An apparatus is provided herein for use in minimally invasive surgical procedures. The apparatus comprises a non-endoscopic portion having first and second actuators, and an endoscopic portion having at least first and second segments connected by at least one angled rotary interface joint. The first segment is operatively connected to the non-endoscopic portion and defines a longitudinal first axis. The second segment includes a distal operating portion actuated by the first actuator and has a lengthwise second axis, the second segment being rotatable in response to actuation of the second actuator around a third axis which is oriented at an angle from the longitudinal first axis of from about 1° to about 60°.

The first segment includes an outer tube and an inner rotary drive tube with a crown gear at its distal end. The second segment includes a proximal bevel gear which engages the crown gear so as to form the angled rotary interface joint.

The rotary drive tube includes a spur gear engaged by a rotary actuator disk in the non-endoscopic portion of the apparatus.

A flexible push rod provides a linkage to actuate the distal operating portion and is driven by a drive cylinder regulated by a trigger actuator. The trigger may be mounted to the body portion or handle grip of the non-endoscopic portion of the apparatus.

The drive cylinder may be pneumatically, hydraulically, electrically, or mechanically powered.

The non-endoscopic portion includes a handle grip which is connected to a body portion by an angled rotary joint. The handle can be rotated from a linearly aligned position to a pistol grip position. A source of power, such as a compressed gas bottle or battery pack may be stored in the handle grip.

A method for using the apparatus is also provided herein.

DETAILED DESCRIPTION OF PREFERRED EMBODIMENT(S)

The apparatus described herein includes features to provide for rotary articulation of the distal endoscopic portion and/or the handle portion. The articulation features may be employed on a variety of endoscopic instruments such as clip appliers, staplers, graspers, tissue retractors, shears, dissectors, manipulators, pushers, and the like.

Figure 1:
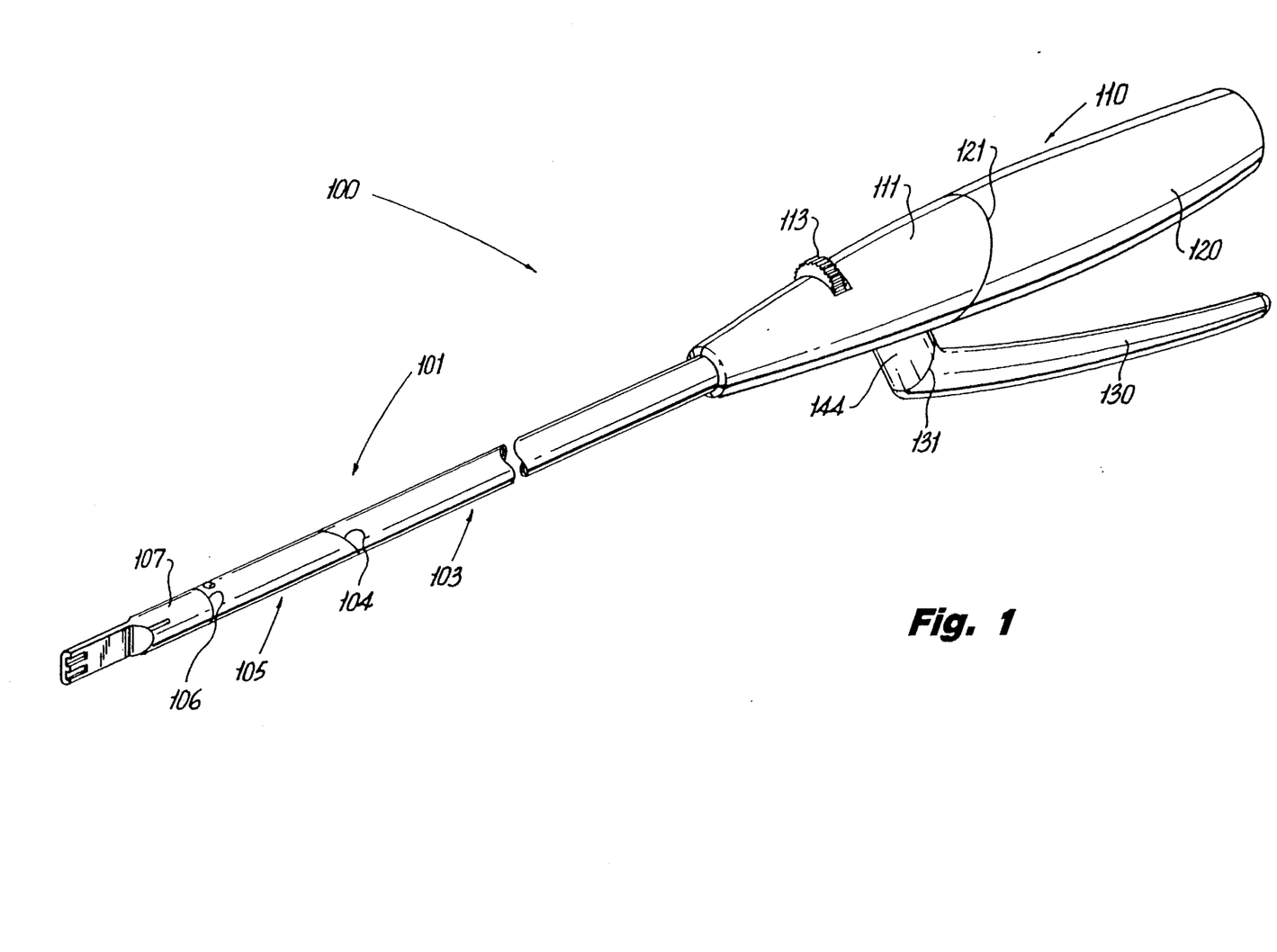
FIG. 1 is a perspective view of the apparatus.
Figure 2:
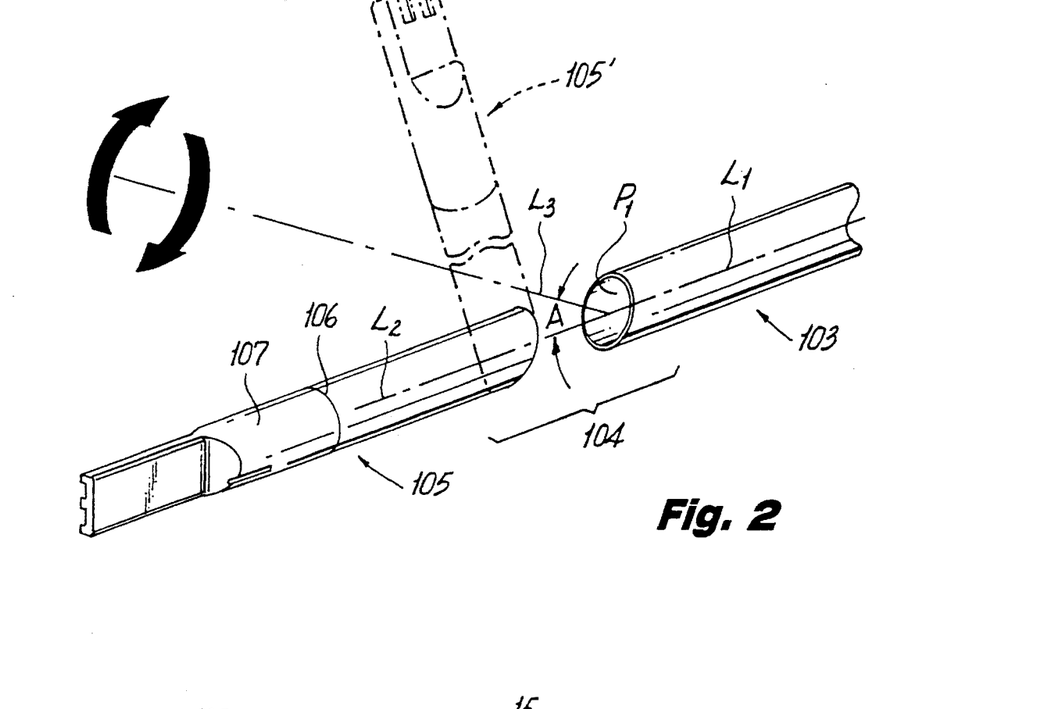
FIG. 2 is a perspective view of the endoscopic portion of the apparatus showing the angled rotary interface.

Referring to FIG. 1, apparatus 100 includes an endoscopic portion 101 and a non-endoscopic handle portion 110. The endoscopic portion is an elongated tubular member comprising a first segment 103, a second segment 105, and a distal operating portion 107. The first segment 103 is connected at its proximal end to the handle portion 110. At its distal end first segment 103 is connected to the proximal end of second segment 105 by a rotatable angled interface, joint 104, which is configured as shown in FIG. 2. The second segment 105 terminates in the distal operating portion 107, which may optionally separately articulate at joint 106. The distal operating portion 107 as shown in this embodiment is a stapler unit disclosed and described in U.S. Pat. No. 5,289,963, herein incorporated by reference. Also, as shown in U.S. Pat. No. 5,289,963 is a mechanism for laterally articulating the stapler unit which may optionally be incorporated into the present apparatus.

Referring to FIG. 2, the angled rotary interface joint 104 joining the first and second segments 103 and 105 is shown. The first segment 103 has a longitudinal axis $L_1$. The second segment 107 is characterized by a longitudinal axis $L_2$. The rotary interface 104 defines a geometric plane $P_1$ which is angled with respect to axis $L_1$. An axis of rotation $L_3$ extends perpendicularly from plane P and is angled from axis $L_1$ at an angle A, wherein A can be from about 1° to about 60°, more preferably from about 40° to about 50°, and most preferably about 45°. As can be seen from FIG. 2, the second segment 105 is rotatable around axis $L_3$ such that the path traced by axis $L_2$ defines a substantially conical geometric surface. At least at one position, the second axis $L_2$ is collinear with axis $L_1$ so that the endoscopic portion 101 is configured as a long, straight tube which can be disposed through a trocar cannula. Once the endoscopic portion 101 has been positioned in a cannula such that the second segment 105 is beyond the distal end of the cannula and located entirely within the body cavity, the second segment 105 may be rotated relative to the first segment 103 in order to configure the second segment 105 at an angle from the first segment 103. For example, referring to FIG. 2, upon rotation the second segment 105 may be moved from its initial collinear position to a position designated as 105' wherein it is angled from the first segment 103. The maximum angle between the position at 105' and the initial collinear position is achieved by 180° rotation of the second segment 105 and is equal to twice the angle A of axis $L_3$. Thus, if axis $L_3$ is angled at 45° from $L_1$, the second segment 105 may be moved to a 90° angle from its original position.

This articulation of the second segment 105 with the distal operating portion presents many advantages. For example it allows the endoscopic portion 101 to be inserted through a cannula, yet also permits the instrument, after insertion, to be configured to angled shapes. This permits the surgeon to gain access to body tissue which is otherwise difficult to reach.

Figure 3:
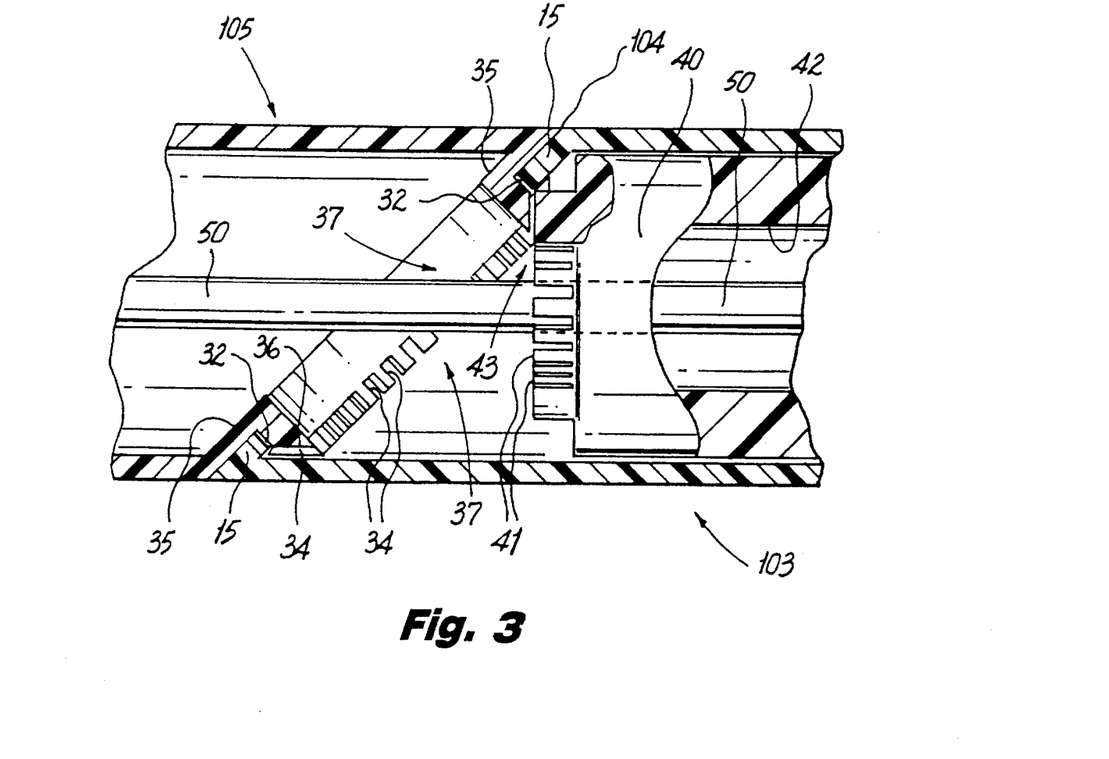
FIG. 3 is a partly sectional side view showing the angled rotary interface in the endoscopic portion of the apparatus.

FIG. 3 illustrates a joint configuration to permit such angled rotation of an endoscopic portion as described above. The second segment 105 possesses at its proximal end an angled annular projection 31 having a circumferential slot 32 extending therearound. Slot 32 is defined by a base portion 35 and a frustoconical bevel gear 36. Central aperture 37 extends through the projection 31 to permit passage therethrough of drive mechanisms and the like. The bevel gear includes slots 34 for engaging corresponding teeth 41 of a rotary driver 40.

The first segment 103 includes an angled annular lip 15 which engages slot 32 to permit rotary movement of the second segment 105 relative to the first segment 103 while these segments remain coupled.

Rotary driver 40 is a tubular member rotatably mounted within the bore of the first segment 103. Rotary driver 40 has a plurality of distally pointing teeth 41 circumferentially disposed around the distal opening of central bore 42 on the drive member to form a crown gear. As can be seen from FIG. 3, the teeth 41 are adapted to engage slots 34 of the bevel gear 36 at a region of juxtaposition 43. When driver 40 is rotated, rotation is conveyed to the second segment 105. The rotary driver may be rotated by the instrument user by means of an actuator ring 113 rotatably mounted to the non-endoscopic portion 110, and having an exterior surface for user actuation as will be discussed below.

A push rod 50 extends longitudinally through the joint and connects an actuator in the handle portion with the distal operating portion 107. Push rod 50 can operate by reciprocating motion or by rotation. It should be super elastic in order to permit flexing at the joint 104 while providing for actuation of the distal operating portion. Various types of metal alloys are known in the art, for example shape memory alloys, may be used to fabricate the push rod 50.

Figure 4:
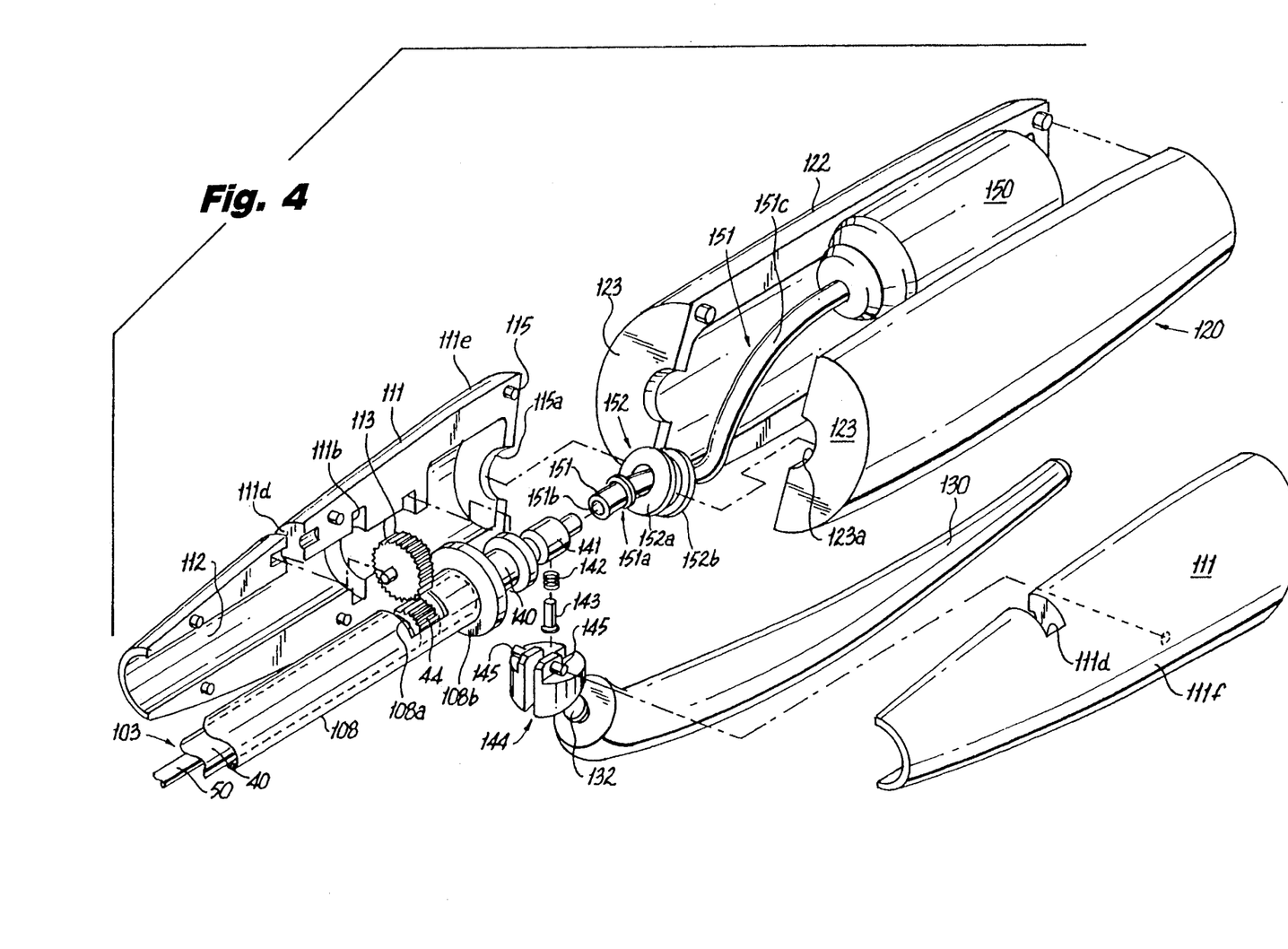
FIG. 4 is an exploded perspective view of the non-endoscopic portion of the apparatus.

Referring now to FIGS. 1 and 4, handle portion 110 includes a body portion 111, a handle grip 120, and trigger 130. The handle grip 120 and trigger 130 both are able to rotatably articulate with respect to body portion 111 by means of angled joints 121 and 131, respectively. The trigger 130 in this embodiment is connected to a projecting trigger mount 144 which is pivotally attached to the body portion 111, as described below.

Figure 5:
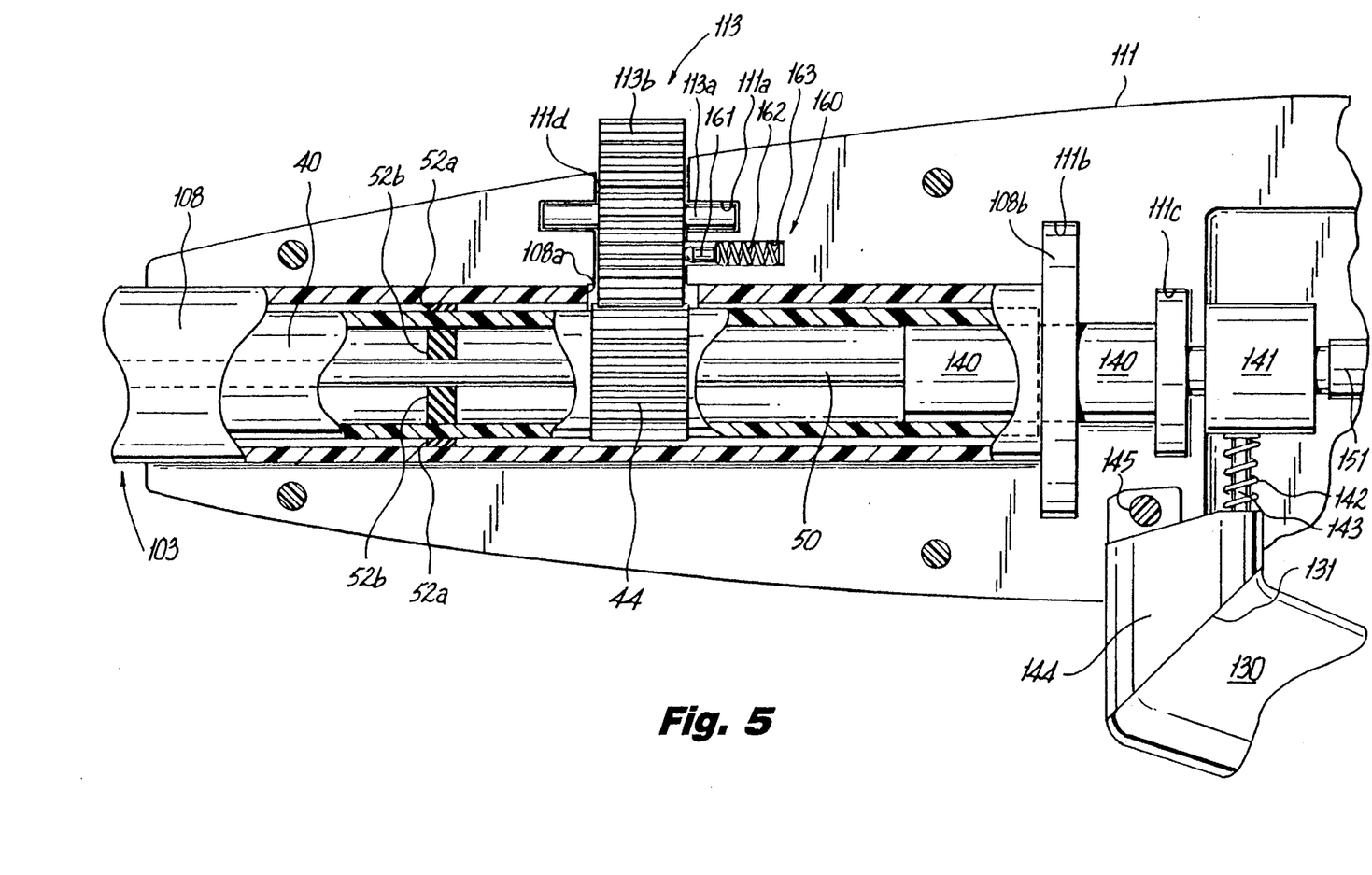
FIG. 5 is a partly sectional side view of the body portion of the apparatus.

Referring now to FIGS. 4 and 5, the body portion 111 may be fabricated as two halves 111e and 111f which may be assembled to form body portion 111 and includes an axial bore 112 in which the proximal end portion of the first segment 103 is disposed. First segment 103 includes the outer tube 108, and the rotary drive tube 40. As mentioned above, the rotary drive tube 40 is a cylindrical member having teeth 41 at its distal end for engaging corresponding slots in the proximal end of the second segment to achieve rotation of the second segment 105, as shown in FIG. 3. In the vicinity of its proximal end the rotary drive tube 40 possesses a circumferential array of longitudinally oriented notches 44 which function as a spur gear. A slot 108a is provided in the outer tube 108 to allow access to the gear 44, with which it is aligned.

Annular seals 52a and 52b prevent the passage of gas or other fluids through the apparatus. Seals 52a and 52b are preferably fabricated from a synthetic polymeric material and may be lubricated with a biocompatible lubricant grease, such as a silicone or a solid lubricant, or they may be self-lubricating by having a low coefficient of friction or by containing a lubricant within the structure of the seal material.

Rotary actuator 113 includes a disk shaped member mounted in slot 111d in the body portion and having axles 113a rotatably mounted within slots 111a in the body portion and aligned in parallel with the axis of the instrument. The upper portion of the disk shaped member of the rotary actuator 113 extends beyond the surface of the body portion 111 to allow actuation by a user's finger. The lower portion of the disk shaped member extends through slot 108a to contact the rotary driver 40. The periphery of the disk portion includes gear teeth 113b which engage the corresponding notches 44 of the rotary driver. Thus, rotation of rotary actuator 113 by the surgeon causes rotation of the rotary drive tube 140, which, in turn, causes rotating articulation of the second segment 105 around angled joint 104.

Optionally, a click-stop feature 160 may be included which comprises a plunger 161 slidably disposed within slot 163 and resiliently biased by spring 162 into engagement with corresponding slots (not shown) arrayed on the proximal surface of disk shaped rotary actuator 113. The distal tip of plunger 161 is rounded to permit disengagement when a sufficient turning force has been applied to rotary actuator 113. The biasing force of the spring 162 is adapted for releasable engagement of the click-stop mechanism 160 by selecting a suitable spring 162 such that the position of the rotary actuator 113 (and second segment 105) is stabilized against free spinning and unintended movement. Movement is easily accomplished when the surgeon actuates the rotary actuator 113, and the click-stop feature 160 provides audible as well as tactile indication when a certain position has been reached.

The proximal end of outer tube 108 includes a flange 108b which is fixedly mounted to a slot 111b in the body portion.

Push rod 50 is operatively connected to drive cylinder 140, which is disposed within bore 112 of the body portion. Drive cylinder 140 preferably is pneumatically powered and has an internal movable piston (not shown) which drives the push rod 50 with a reciprocating motion for actuating the distal operating portion 107. Optionally, a rotary motion can be employed, preferably in conjunction with a linear cam or barrel cam. Suitable pneumatic drive cylinder devices are known to those with skill in the art and are commercially available.

The pneumatic drive cylinder 140 is controlled by switching unit 141 which includes a valve mechanism. Plunger 143 is mounted to the switching unit and operates a valve for controlling the flow of compressed gas to drive pneumatic cylinder 140. Plunger 143 is resiliently biased by spring 142 to a closed-valve position. Trigger mount 144 is pivotally mounted to body portion 111 by means of pivot pins 145.

Trigger 130 is an elongated member having a projection 132 adapted for rotatable engagement with a corresponding slot in trigger mount 144 such that trigger 130 may be pivoted with respect to trigger mount 144.

The cam member 144 includes a bottom surface 146 which is angled with respect to the longitudinal axis of the body portion 111. Likewise, the trigger 130 includes a surface 132 angled with respect to the lengthwise extension of the trigger. Surfaces 132 and 146 are in slidable contact to form angled rotary interface 131. Pivoting trigger 130 around an axis of rotation defined by projection 132 will move trigger between differently angled positions with respect to body portion 111, as discussed in further detail below.

Pressing of the trigger 130 causes trigger mount 144 to pivot around pins 145 and contact the plunger 143. Further pressing of the trigger moves the plunger 143 against the biasing force of spring 142 to open the valve in drive switching unit 141. This permits the flow of compressed gas to drive the pneumatic drive cylinder 140.

The compressed gas may be provided by a compressed gas storage bottle 150 mounted in the interior of handle grip 120. The handle grip 120 is an elongated generally cylindrical member 122 which may be fabricated as two mating halves 122a and 122b which join to form an enclosure for mounting the gas bottle 150. A flexible tube 151 extends from the gas bottle 150 through axial bore 152c in the rotatable coupling 152 to switching unit 141 and carries compressed gas thereto. Tube 151 possesses a rotating seal 151a which permits tube portions 151b and 151c to rotate relative to each other without the tube 151 pinching closed.

Body portion 111 possesses a proximal wall 115 oriented at an angle with respect to the longitudinal axis of the body portion. Handle grip 120 possesses a distal wall 123 which is oriented at an angle with respect to the longitudinal axis of the handle grip. Walls 115 and 123 face each other in sliding contact so as to form an angled rotary interface 121 similar in operational features to rotary interface 104. That is, handle grip 120 may be rotated relative to body portion 111 to move from a position in linear alignment with the body portion 111, as shown in FIG. 4, to a position in which it is angled from the body portion, as shown in FIGS. 6 and 7.

To permit rotation around rotary interface 121 a rotatable coupling 152 is provided. Coupling 152 is disposed through centrally located apertures 123a and 115a in the distal and proximal walls 123 and 115, respectively, and possesses circumferential flanges 152a and 152b which abut the inner surfaces of the facing walls 115 and 123 in the vicinity of apertures 115a and 123a. Thus, wall 123 of the handle grip 100 and wall 115 of the body portion are held in slidable contact and are rotatable with respect to each other around an axis defined by the rotatable coupling 152. Rotatable coupling 152 also possess a central bore 152c through which tube 151 is disposed.

Figure 6:
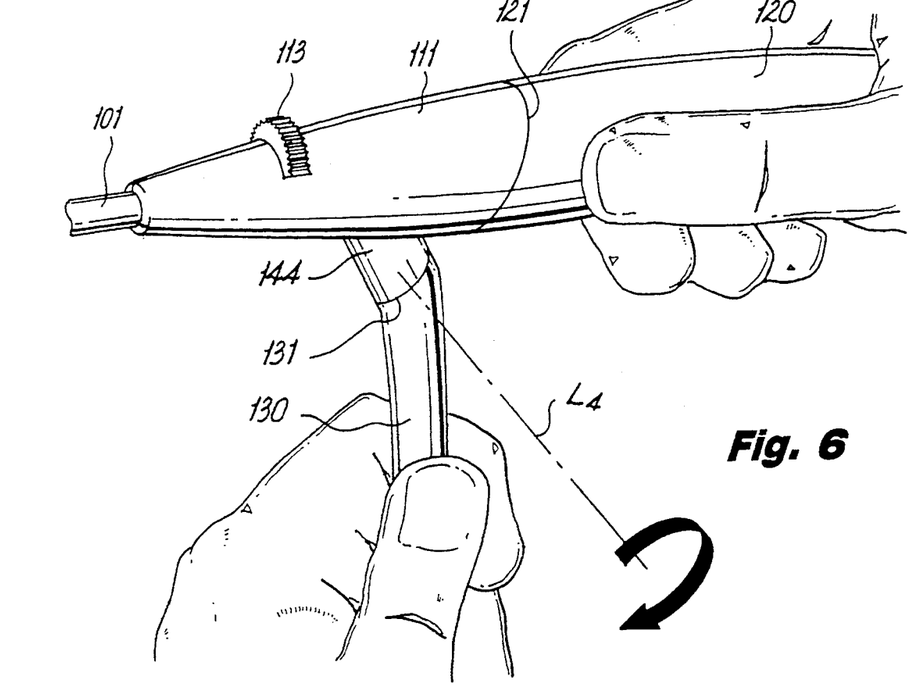
FIGS. 6 and 7 are perspective views illustrating the reconfiguration of the handle portion of the apparatus by rotation.
Figure 7:
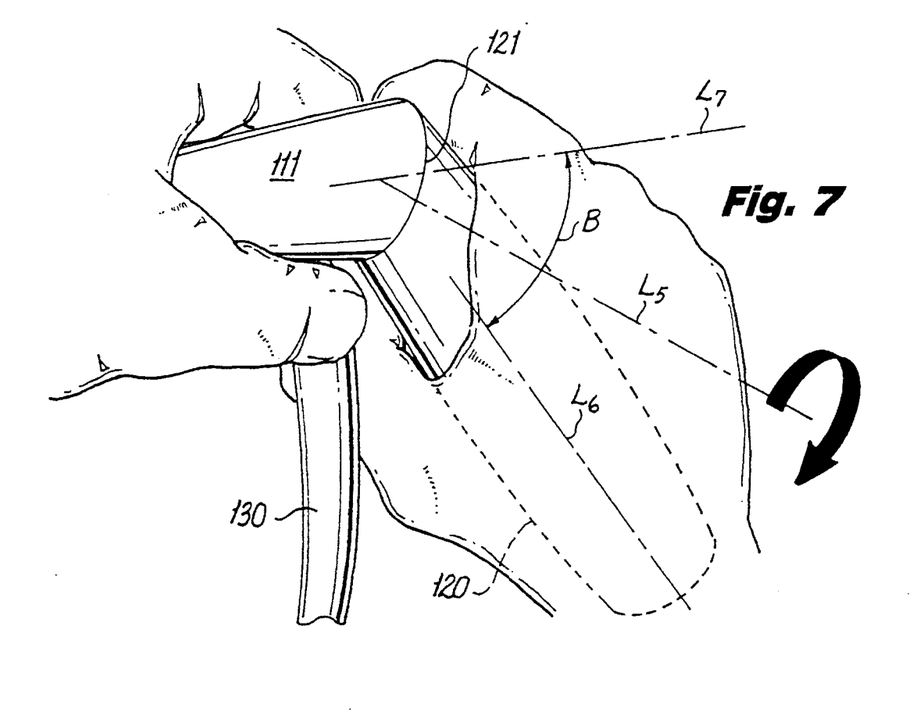

Referring now to FIGS. 6 and 7, the articulation of the handle and trigger are illustrated. As shown in FIG. 6 the trigger 130 may be rotated around axis $L_4$ which is defined by projection 132 (FIG. 4) and which extends perpendicularly through the plane defined by rotatable interface 131 (FIG. 5). Thus, the surgeon can easily maneuver the trigger 130 from an orientation as shown in FIG. 4, wherein the trigger extends in a generally linearly aligned, or horizontal (as shown) direction, to an orientation as shown in FIG. 6, wherein the trigger is moved to a more vertical configuration.

Next, as shown in FIG. 7, the handle grip 120 is rotated around axis $L_5$, which is defined by a straight line extending perpendicularly through the plane defined by rotary interface 121. The body portion 111 is characterized by axis $L_7$, which is collinear with axis $L_1$ of the first segment 103. Thus the surgeon can easily move the handle grip 120 from an orientation aligned with the axis $L_1$ of endoscopic portion as shown in FIG. 6 to the angled "pistol grip" orientation shown in FIG. 7. In the "pistol grip" orientation the handle grip axis $L_6$ is angled from the body portion axis $L_7$ by angle B, wherein angle B can range from about 1° to about 90°.

Figure 8:
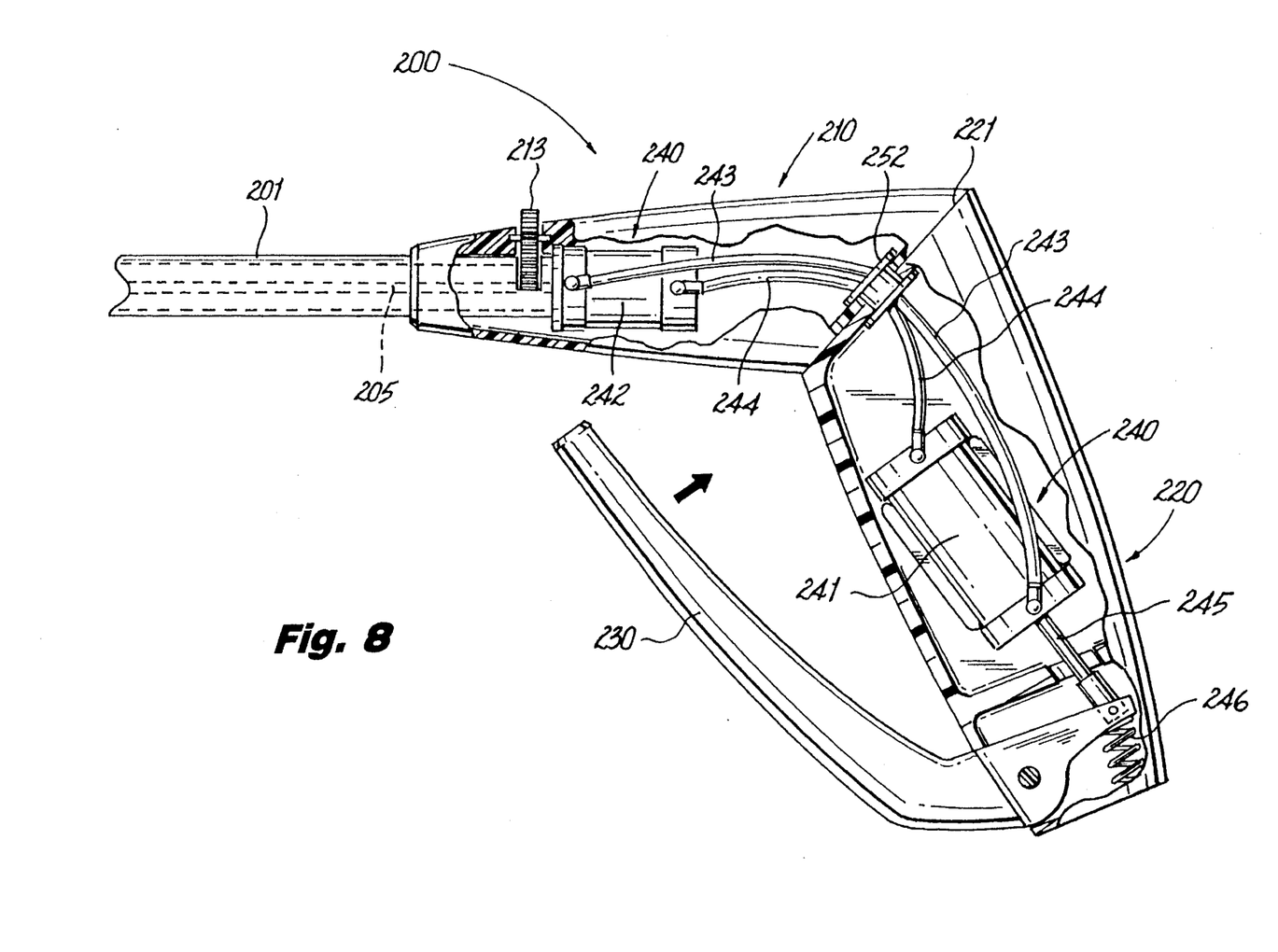
FIG. 8 is a partly sectional side view of an alternative embodiment of the apparatus.

Referring now to FIG. 8, an alternative embodiment 200 of the apparatus is shown wherein the trigger 230 is hingedly connected to the rear portion of the handle grip 220.

Handle grip 220 and body portion 210 are pivotally connected at rotary interface 221 by means of a coupling 252, such as coupling 152 described above.

Endoscopic portion 201 is similar in operation to endoscopic portion 101 and is similarly actuated by means of rotary actuator 213.

An alternative hydraulically operated actuation mechanism 240 is employed, which comprises first and second cylindrical hydraulic chambers 241 and 242 containing a hydraulic fluid such as water, oil or other suitable liquid, and connected by means of two fluid carrying tubes 243 and 244.

A movable piston (not shown) is located in the interior of each hydraulic chamber. The piston in the first hydraulic chamber 241 is mechanically linked to trigger 230 by means of rod 245. The pistol in the second hydraulic chamber 242 is mechanically linked to drive rod 205 for actuating the distal operating portion of the apparatus. When the apparatus 200 is actuated by pressing trigger 230, the trigger 230 pivots (clockwise, as shown) around pivot pin 231 and moves rod 245 out of first chamber 241, thereby forcing hydraulic fluid through tube 243 and into the distal end of the second chamber 242. The piston in the second chamber 242 is forced to move proximally, thereby pulling the drive rod 205 proximally and actuating the distal operating portion. Fluid exits the second hydraulic chamber 242 via line 244 and enters the first hydraulic chamber 241. Alternative configurations of the hydraulic tubes may be employed to move the drive rod distally instead of proximally. Also, hydraulic chamber 242 may alternatively incorporate a hydraulically driven rotor to turn drive rod 205 rather than move it linearly. Optionally, a spring 246 may be employed to bias the trigger 230 back to its initial position.

As with the previously described embodiment the handle grip 220 may be pivoted at rotary interface 221 between linearly aligned and pistol grip positions.

Figure 9:
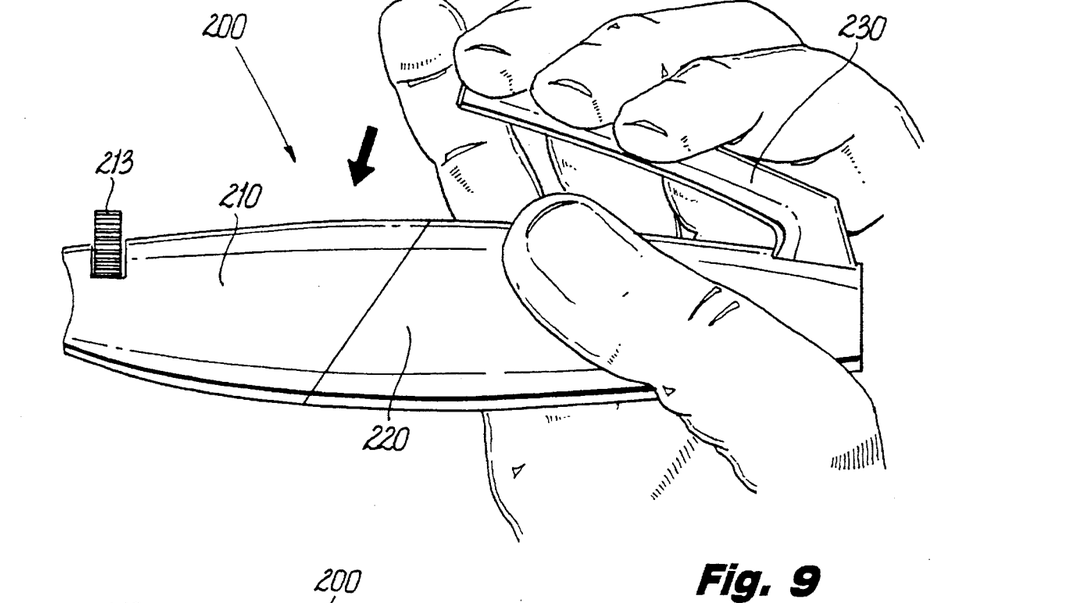
FIGS. 9 and 10 are side views illustrating the reconfiguration of the handle grip portion of the apparatus.
Figure 10:
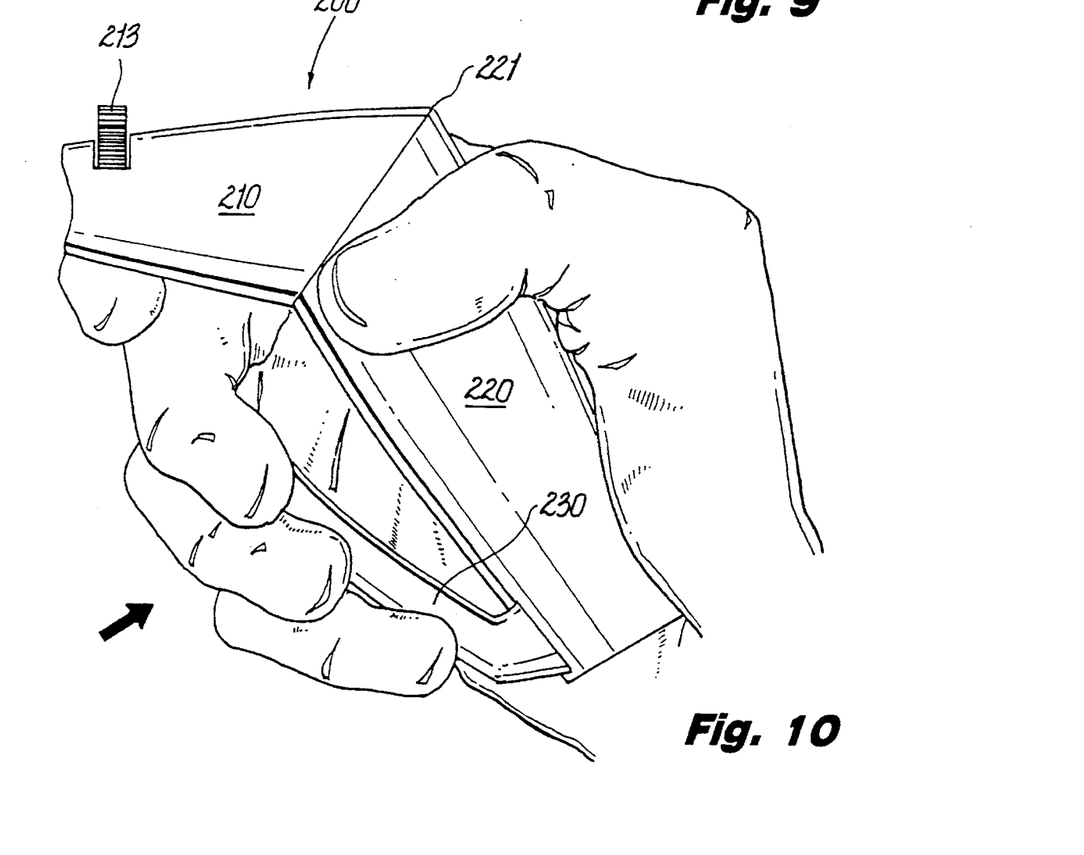

FIGS. 9 and 10 illustrate the alternative configurations of the apparatus 200. In FIG. 9, the handle grip 220 is linearly aligned with the body portion 210. However, rotation of handle grip 220 around rotary interface 221 reorients it to a pistol grip, as shown in FIG. 10.

One skilled in the art will recognize that other methods of powering the apparatus may be employed. For example the drive motor may be electrically operated and the handle grip may contain a battery pack to provide a source of electric current regulated by a switch or potentiometer controlled by the trigger. Also, as an alternative, the trigger may operate mechanical linkages such as gears, racks and pinions, cables, and the like to drive the instrument. Such alternatives are easily accomplished by those skilled in the art with available materials and commonly known techniques.

Figure 11:
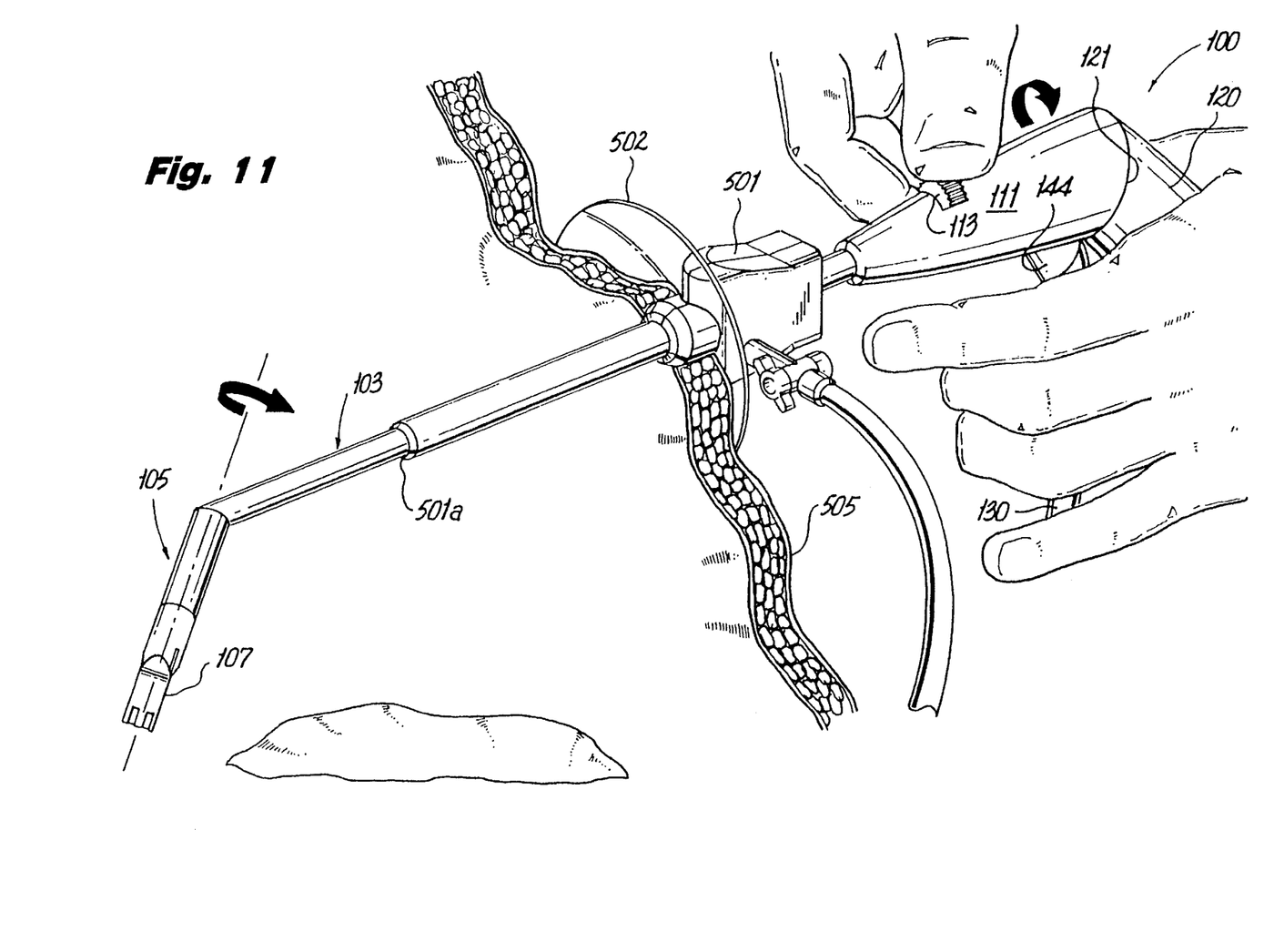
FIG. 11 is a perspective view illustrating the use of the present apparatus in an endoscopic surgical procedure.

Referring now to FIG. 11, a method of using the present apparatus is illustrated. A cannula assembly 501 such as commonly used in endoscopic procedures is stabilized by a patch 502 and inserted through an incision in a wall of body tissue 505. Apparatus 100 is inserted through the cannula assembly 501 until the second segment 105 is fully within the body cavity and beyond the distal end 501a of the cannula.

To position the distal operating portion 107 the surgeon turns actuator 113 to angle the second segment 105. The distal operating portion 107 may then be actuated by pressing trigger 130.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended hereto.

What is claimed is:

1. An apparatus for use in minimally invasive surgical procedures, which comprises:

a) non-endoscopic portion; and b) an endoscopic portion having at least first and second segments connected by at least one angled rotary interface joint, wherein the first segment is operatively connected to said non-endoscopic portion and defines a longitudinal first axis, the rotary interface joint defining a plane oriented at a fixed angle with respect to the longitudinal first axis, and wherein the second segment includes a distal operating portion and has a lengthwise second axis, said second segment being rotatable around a third axis which is oriented at an angle from the longitudinal first axis of from about 1° to about 60°, wherein the second axis traces out a conical geometric surface when said second segment is rotated around the third axis at least one position of the second axis being collinear with the first axis.

2. The apparatus of claim 1 wherein the third axis is perpendicular to the plane defined by the rotary interface joint.

3. The apparatus of claim 1 wherein said first segment comprises an outer tube and a rotary drive tube rotatably disposed within said outer tube, said rotary drive tube having an axial bore and a distal end with an array of distally pointing teeth forming a crown gear.

4. An apparatus for use in minimally invasive surgical procedures, which comprises:

a) a non-endoscopic portion; and b) an endoscopic portion having at least first and second segments connected by at least one angled rotary interface joint, wherein the first segment is operatively connected to said non-endoscopic portion and defines a longitudinal first axis, and wherein the second segment includes a distal operating portion and has a lengthwise second axis, said second segment being rotatable a round a third axis which is oriented at an angle from the longitudinal first axis of from about 1° to about 60°, wherein said first segment comprises an outer tube and a rotary drive tube rotatably disposed within said outer tube, said rotary drive tube having an axial bore and a distal end with an array of distally pointing teeth forming a crown gear, and wherein said second segment possesses an outer tube having a proximal end with an array of proximally pointing teeth forming a bevel gear, at least a portion of said bevel gear teeth being engaged with at least some of said crown gear teeth of said rotary device tube such that rotation of said rotary drive tube effects rotation of said outer tube of said second segment.

5. The apparatus of claim 4 wherein said non-endoscopic portion of said apparatus comprises a body portion including a housing having an interior longitudinal bore.

6. The apparatus of claim 5 wherein said first segment of said endoscopic portion has a proximal end portion disposed within said bore of said body portion housing, said body portion including a rotary actuator disk rotatably mounted to said housing and operatively engaged with said rotary drive tube such that rotation of said rotary actuator disk effects rotation of said rotary drive tube.

7. The apparatus of claim 6 wherein said rotary drive tube possesses a circumferential array of teeth forming a first spur gear and said outer tube possesses a slot aligned with said array of teeth in said rotary drive tube, said rotary actuator disk possessing circumferential teeth forming a second spur gear, at least a portion of said rotary actuator disk being disposed through said slot in said outer tube so as to engage said first and second spur gears.

8. The apparatus of claim 5 wherein said body portion has a longitudinal fourth axis defined by said bore, said fourth axis being collinearly aligned with said longitudinal first axis, and said non-endoscopic portion further includes a handle grip portion having a longitudinal fifth axis, said body portion and handle grip portion being rotatably connected at an angled rotary interface.

9. The apparatus of claim 8 wherein said handle grip is rotatable between a first position wherein said longitudinal fifth axis and said longitudinal fourth axis are collinearly aligned, and a second position wherein said fifth longitudinal axis is oriented at an angle from said fourth longitudinal axis.

10. The apparatus of claim 9 wherein said angle between said fifth longitudinal axis and said fourth longitudinal axis is between about 1° and about 90°.

11. The apparatus of claim 8 wherein said second segment includes a distal operating portion, and said apparatus further includes a drive cylinder and a push rod, said push rod extending through said endoscopic portion and operatively connected between said distal operating portion and said drive cylinder.

12. The apparatus of claim 11 wherein said push rod is linearly moved by said drive cylinder for actuating said distal operating portion.

13. The apparatus of claim 12 wherein said push rod is flexible.

14. The apparatus of claim 11 wherein said push rod is rotatably moved for actuating said distal operating portion.

15. The apparatus of claim 11 wherein said drive cylinder is pneumatically driven, and said handle grip includes a source of compressed gas.

16. The apparatus of claim 11 wherein said drive cylinder is hydraulically driven.

17. The apparatus of claim 11 further including a trigger for actuating said drive cylinder.

18. The apparatus of claim 17 wherein said body portion includes a pivotally connected trigger mount, and said trigger is rotatably connected to said trigger mount at an angled rotary interface.

19. The apparatus of claim 18 wherein said trigger is pivotally mounted to said handle grip.

20. A method for surgically operating on body tissue in the interior of a body cavity, comprising:
   a) creating a puncture incision in a wall of body tissue;
   b) inserting a cannula assembly through said incision;
   c) providing an apparatus which includes
      i) a non-endoscopic portion having first and second actuators,
      ii) an endoscopic portion having at least first and second segments connected by at least one angled rotary interface joint, wherein the first segment is operatively connected to said non-endoscopic portion and defines a longitudinal first axis, the rotary interface joint defining a plane at a fixed angle with respect to the longitudinal first axis, and wherein the second segment includes a distal operating portion actuated by said first actuator and has a lengthwise second axis, said second segment being rotatable in response to actuation of said second actuator around a third axis which is oriented at an angle from the longitudinal first axis of from abut 1 degree to about 60 degrees wherein said second axis traces out a conical geometric surface when said second segment is rotated around the third axis at least one position of the second axis being collinear with the first axis;
   inserting said endoscopic portion of said apparatus through said cannula assembly in the body cavity;
   positioning said distal operating portion at an operating site;
   actuating said distal operating portion.

21. The method of claim 20 wherein positioning said distal operating portion includes actuating said second actuator for rotating said second segment to a position wherein said second axis is angled with respect to said first axis.

* * * * *